United States Patent [19]
Awtry et al.

[11] Patent Number: 4,790,198
[45] Date of Patent: Dec. 13, 1988

[54] GRAIN PROBE

[76] Inventors: Jon Awtry, 1411 Victoria; Dennis R. Heflin, Rte. 4, Box 211A, both of Harlan, Iowa 51537

[21] Appl. No.: 96,518

[22] Filed: Sep. 11, 1987

[51] Int. Cl.⁴ .............................................. G01N 1/12
[52] U.S. Cl. ................................................. 73/864.64
[58] Field of Search ........... 75/864.64, 864.63, 864.51, 75/863.31

[56] References Cited

U.S. PATENT DOCUMENTS

| | | | |
|---|---|---|---|
| 460,666 | 10/1891 | Stacy | 73/863.31 |
| 902,049 | 10/1908 | Bonnell | 73/864.64 |
| 1,078,847 | 11/1913 | Grauenfels | 73/863.31 |
| 1,256,413 | 2/1918 | Wiswell | 73/864.64 |
| 3,065,637 | 11/1962 | Landes | 73/863.31 |
| 3,091,968 | 6/1963 | Platzer | 73/863.31 |
| 3,218,869 | 11/1965 | Fields et al. | 73/863.31 |
| 4,072,059 | 2/1978 | Hamilton | 73/864.64 |
| 4,359,110 | 11/1982 | Peterson | 175/20 |

FOREIGN PATENT DOCUMENTS

| | | | |
|---|---|---|---|
| 0309276 | 7/1971 | U.S.S.R. | 73/864.64 |
| 0386893 | 1/1933 | United Kingdom | 73/864.64 |

*Primary Examiner*—Stewart J. Levy
*Assistant Examiner*—Robert R. Raevis
*Attorney, Agent, or Firm*—Zarley, McKee, Thomte Voorhees & Sease

[57] ABSTRACT

A grain probe comprising an inner tubular member mounted within an outer tubular member with the tubular members having openings formed therein which may be moved into registering alignment so that grain may enter the interior of the inner tubular member. The inner tubular member is divided into a plurality of grain compartments which are separated by partitions. The inner tubular member is also selectively slidably mounted within the outer tubular member so that grain may be successively dumped from individual grain compartments after the probe has been removed from the grain.

3 Claims, 5 Drawing Sheets

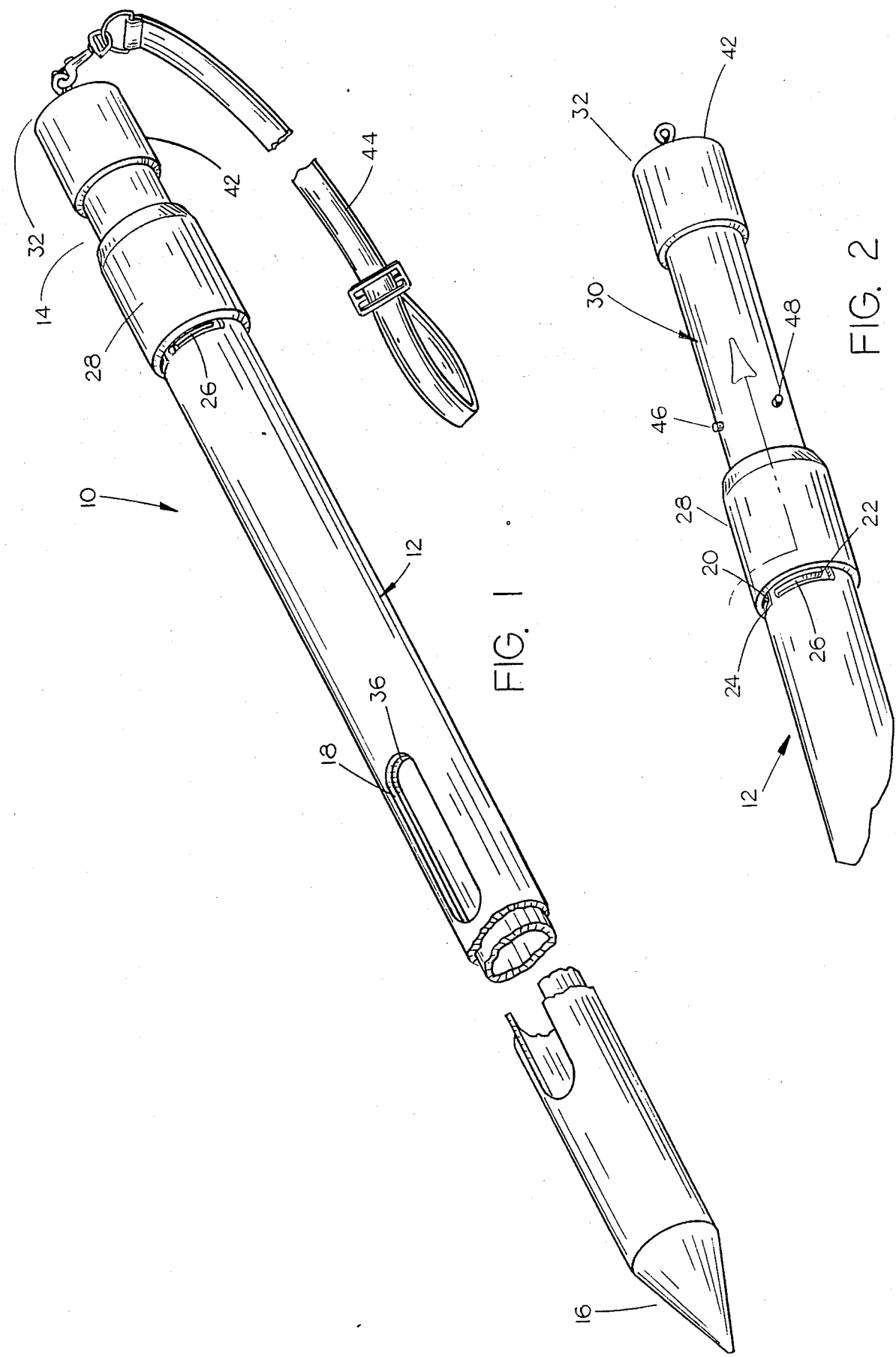

GRAIN PROBE

BACKGROUND OF THE INVENTION

This invention relates to a grain probe and more particularly to a grain probe which enables grain to be sampled at various depths within a grain storage area.

Grain probes have long been used to sample grain in grain storage facilities such as granaries or the like. Conventional grain probes consist of an elongated outer tubular member having an inner tubular member rotatably mounted therein. The tubular members have a plurality of vertically spaced openings formed therein which may be moved into registering alignment after the probe has been inserted into the grain so that the grain can enter the interior of the probe. The inner tubular member is then rotated with respect to the outer tubular member to seal the material within the probe. The probe is then removed from the grain and the inner tubular member again rotated with respect to the outer tubular member so that the openings in the tubular members are again in registering alignment so that the grain may be dumped from the probe. The grain is normally dumped into a tarpaulin or the like since all of the openings are opened simultaneously which causes grain to be dumped from the entire length of the probe.

Not only is the dumping of the grain from the probe inconvenient, but the grain from the entire length of the probe is dumped onto the tarpaulin which makes it difficult, if not impossible to determine the status of the grain at various depths in the granary. This is so because the grain tends to mingle on the tarpaulin thereby making it difficult to ascertain the depth from which the grain was derived.

It is therefore a principal object of the invention to provide an improved grain probe.

Yet another object of the invention is to provide a grain probe including inner and outer tubular members wherein the inner tubular member is provided with a plurality of vertically spaced compartments with the inner tubular member being rotatably mounted within the outer tubular member and longitudinally slidably mounted therein so that the individual compartments may be successively dumped.

Yet another object of the invention is to provide a grain probe which enables grain at various depths within a granary or the like to be sampled.

Still another object of the invention is to provide a grain probe which is economical of manufacture, durable in use and refined in appearance.

BRIEF DESCRIPTION OF THE DRAWINGS

FIG. 1 is a partial perspective view of the grain probe of this invention:

FIG. 2 is a partial perspective view illustrating the inner tubular member being pulled outwardly from the outer tubular member:

SUMMARY OF THE INVENTION

Figure 3:
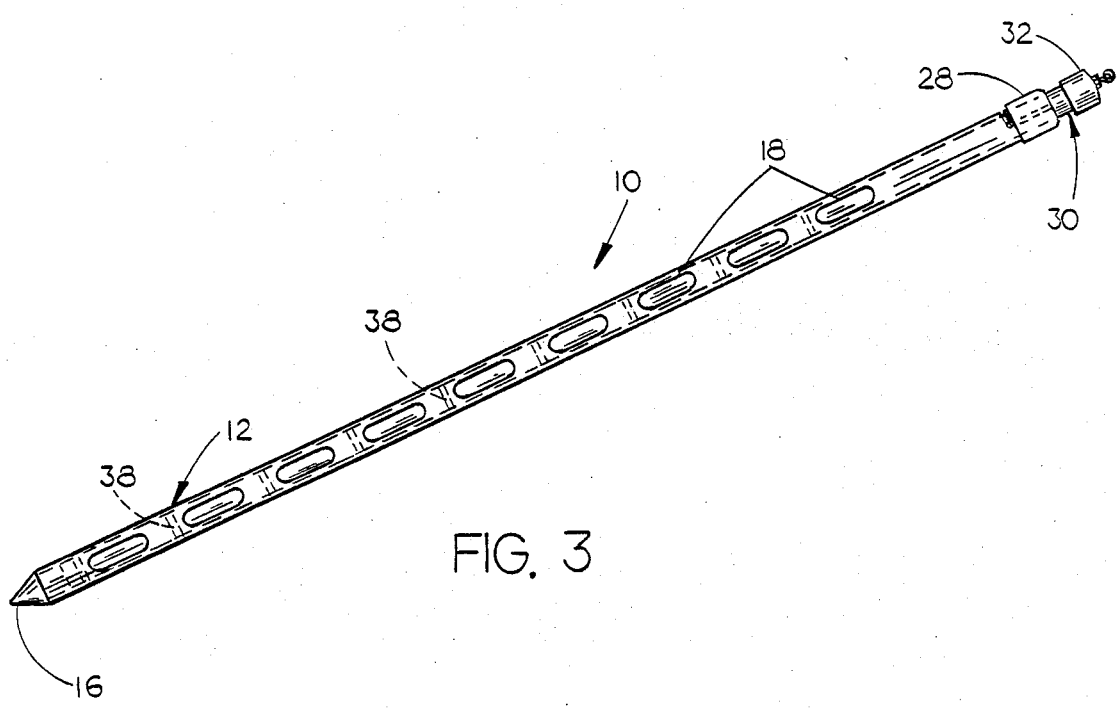
FIG. 3 is a plan view of the grain probe.
Figure 4:
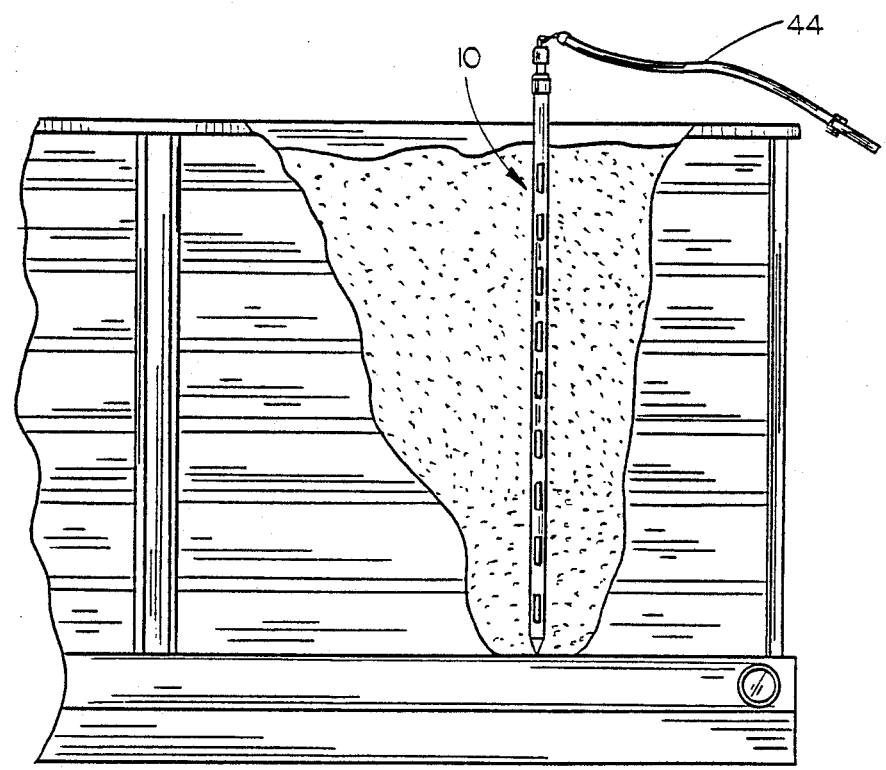
FIG. 4 is a side view illustrating the grain probe of this invention being inserted downwardly into grain stored within a grain storage area.
Figure 5:
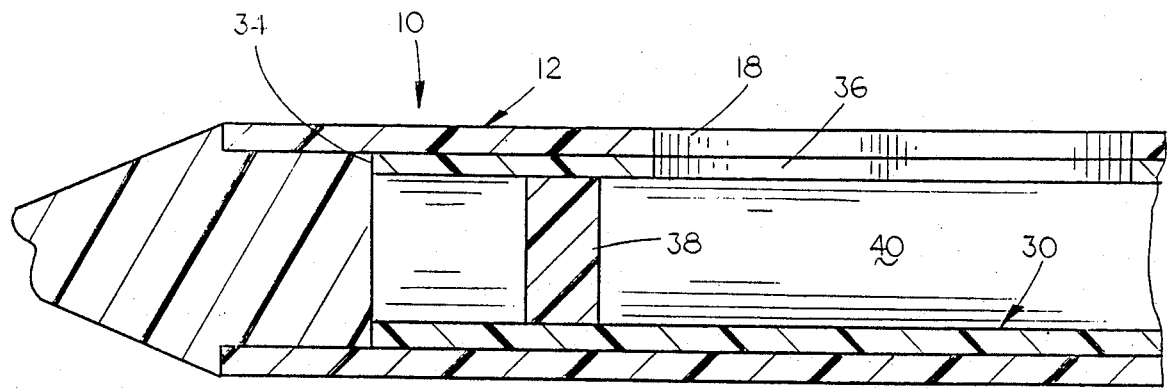
FIG. 5 is a partial longitudinal sectional view of the grain probe.
Figure 6:
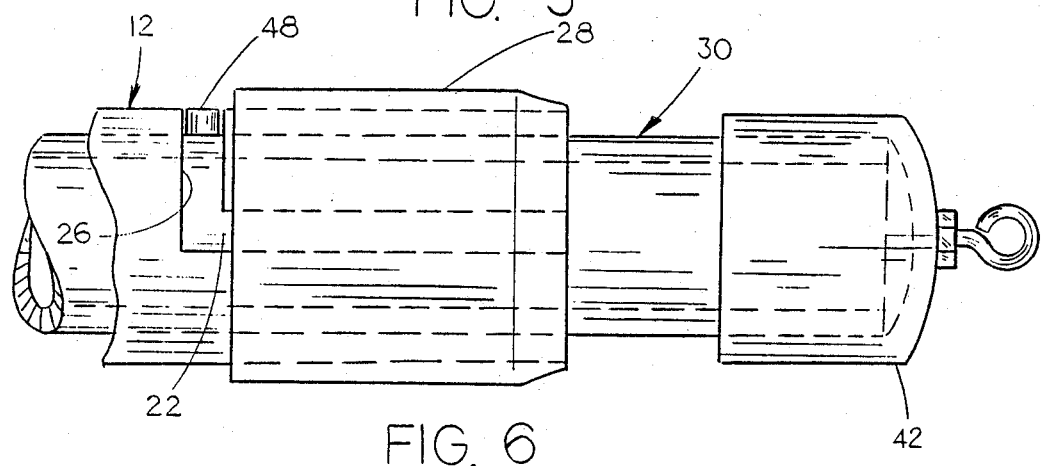
FIG. 6 is a partial elevational view of the upper end of the grain probe wherein the tubular members are positioned in the relationship of FIG. 5.
Figure 7:
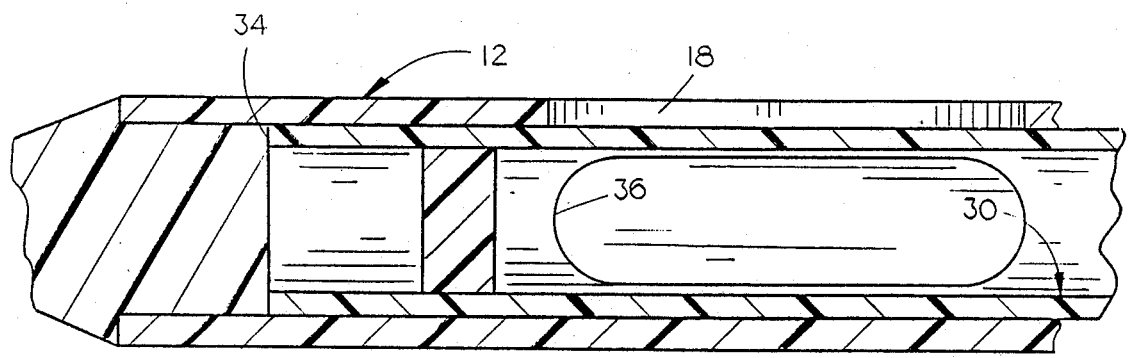
FIG. 7 is a sectional view similar to FIG. 5 except that the inner tubular member has been rotated to a closed position with respect to the outer tubular member.
Figure 8:
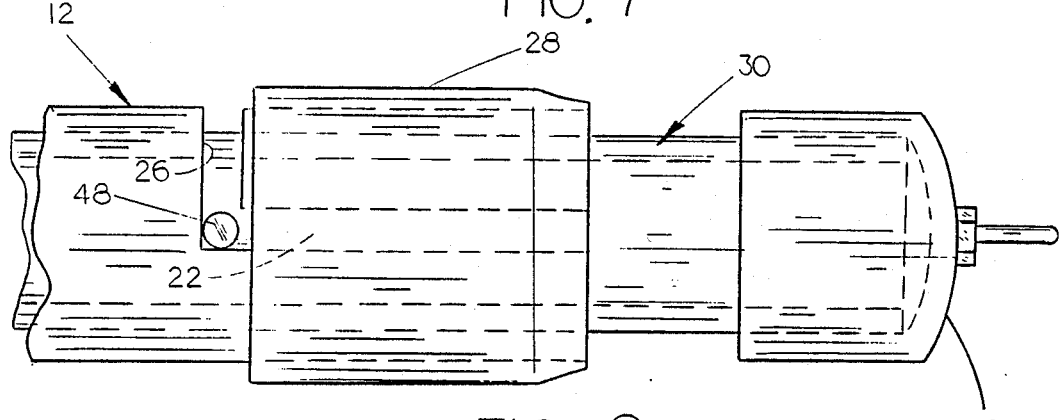
FIG. 8 is a view similar to FIG. 6 but which illustrates the relationship of the tubular members when the tubular members have been rotated to the relative position of FIG. 7.
Figure 9:
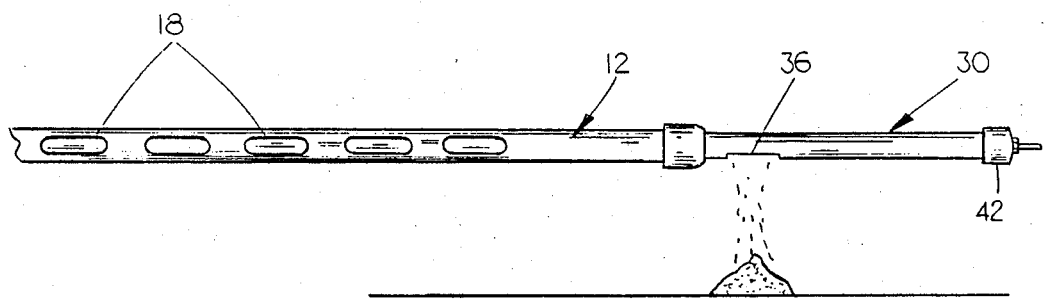
FIGS. 9–11 are side views illustrating the manner in which the grain may be dumped from individual compartments within the inner tubular member.
Figure 10:
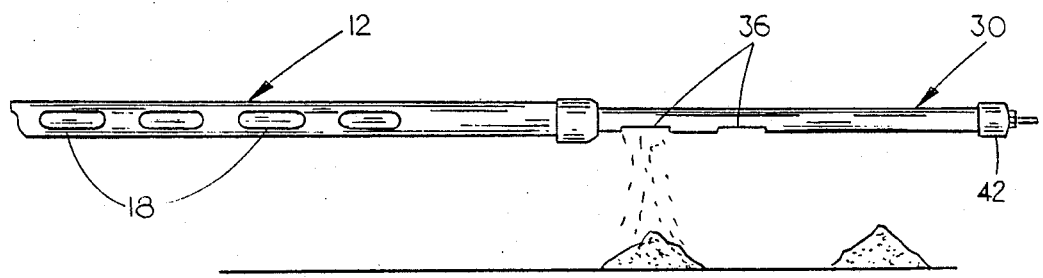
Figure 11:
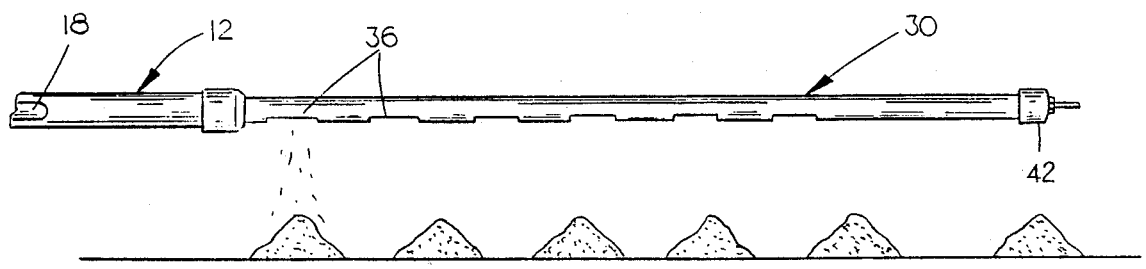
Figure 12:
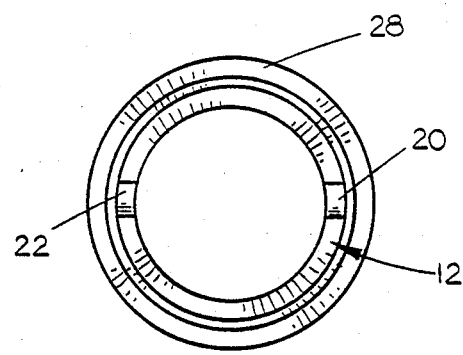
FIG. 12 is an end view of the outer tubular member.
Figure 13:
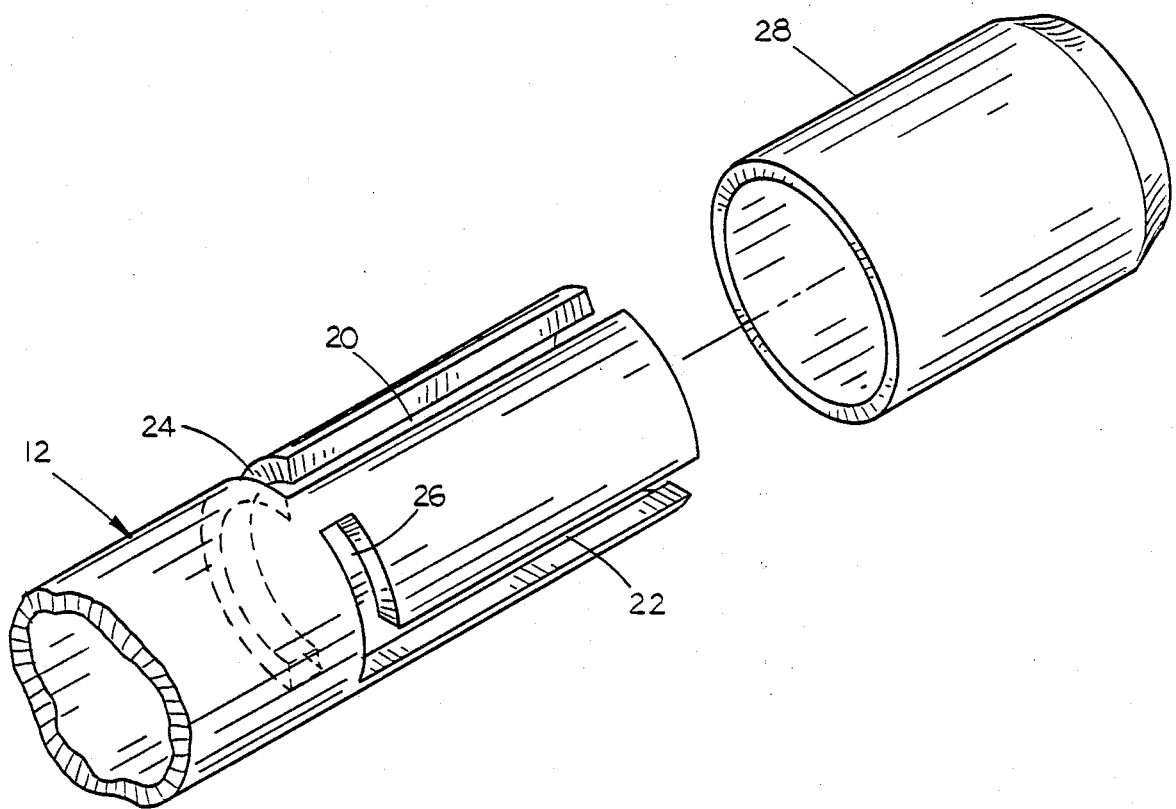
FIG. 13 is a partial exploded perspective view of the upper end of the outer tubular member.

The grain probe of this invention comprises an outer tubular member having an inner tubular member longitudinally slidably mounted therein and also rotatably mounted therein. The outer tubular member has a plurality of vertically spaced openings formed therein extending between the upper and lower ends thereof. The inner tubular member also has a plurality of vertically spaced openings formed therein which may be moved into registering engagement with the openings in the outer tubular member at times to permit grain to enter the interior of the probe when the probe has been inserted into the grain to be sampled. The inner tubular member is divided into a plurality of individual grain compartments which are created by partitions created between adjacent pairs of the openings. After the probe has been inserted into the grain, the inner tubular member is rotated with respect to the outer tubular member to bring the openings into registering alignment with each other so that grain enters the probe. After the probe has been filled with grain, the inner tubular member is rotated with respect to the outer tubular member to maintain the grain in the individual compartments in the inner tubular member. The grain probe is then removed from the grain. The inner tubular member is then longitudinally slidably moved with respect to the outer tubular member to permit each of the grain compartments to be successively dumped.

DESCRIPTION OF THE PREFERRED EMBODIMENT

The grain probe of this invention is referred to generally by the reference numeral 10. Grain probe 10 includes an outer tubular member 12 having an open upper end 14 and a closed, pointed lower end 16. Tubular member 12 is provided with a plurality of vertically spaced openings 18 formed therein at one side thereof as seen in the drawings.

Tubular member 12 is provided with a pair of opposed slots 20 and 22 formed therein which extend downwardly from the upper end thereof. The lower end of slot 20 is in communication with the horizontally extending slot 24 which extends partially around the tubular member 12 as also seen in the drawings. The lower end of slot 22 is in communication with a horizontally extending slot 26 which also extends partially around tubular member 12. Cap 28 is mounted on the upper end of tubular member 12 above slots 24 and 26 so as to almost completely cover slots 20 and 22.

An inner tubular member 30 is rotatably and longitudinally slidably mounted within tubular member 12. For purpose of description, inner tubular member 30 will be described as having an upper end 32 and a lower end 34.

Tubular member 30 is provided with a plurality of vertically spaced-apart openings formed therein which are adapted to register with the openings 18 as will be described in more detail hereinafter. A wall or partition 38 is provided within tubular member 30 between adjacent pairs of openings 36 to create individual grain compartments 40 inwardly of each of the openings 36. Cap 42 is mounted on the upper end of tubular member 30 and has a carrying strap 44 secured thereto. A pair of pins 46 and 48 extend laterally outwardly from tubular member 30 below the upper end thereof. When tubular member 30 is being inserted into tubular member 12, pins 46 and 48 are received by the slots 20 and 22 respectively. Continued inward movement of tubular member 32 with respect to tubular member 12 causes the pins 46 and 48 to move downwardly in slots 20 and 22 until pins 46 and 48 are at one end of the slots 24 and 26. When the pins 46 and 48 are at the lowermost portions of slots 20 and 22, respectively, and are at one end of the slots 24 and 26, respectively, openings 36 do not register with openings 18. There is sufficient friction between the pins 46 and 48 and the interior of the cap 28 to prevent the inadvertent separation of tubular member 30 from tubular member 12. If desired, spring-loaded detent pins or the like could be substituted for the pins 46 and 48.

The probe of this invention is used as follows. Probe 10 is inserted downwardly into the grain to be sampled with the openings 36 and 18 being out of registration so that grain cannot enter the interior of tubular member 30 until the probe has been inserted into the grain to the desired depth. After the probe 10 has been inserted, tubular member 30 is rotated with respect to tubular member 12 with such rotational movement causing the pins 46 and 48 to move in the slots 24 and 26 until the pins 46 and 48 reach the outer ends of the slots 24 and 26, respectively. When the pins 46 and 48 reach the other ends of the slots 24 and 26, respectively, openings 36 register with openings 18 so that grain can pass therethrough into each of the individual grain compartments 40. Tubular member 30 is then rotated with respect to tubular member 12 so that the pins 46 and 48 return to the other ends of the slots 24 and 26, respectively, which closes the openings 18. Probe 10 is then removed from the grain. Inner tubular member 30 is then longitudinally slidably moved with respect to tubular member 12 which causes the pins 46 and 48 to move upwardly in the slots 20 and 22. Tubular member 30 is longitudinally moved with respect to the tubular member 12 until the uppermost opening 36 in the corresponding grain compartment 40 is exposed. The grain is then dumped from the particular grain compartment 40 into a suitable container for testing. When the grain has been dumped from the uppermost grain compartment 40, tubular member 30 is then longitudinally moved with respect to tubular member 12 to expose the grain compartment 40 located immediately below the same compartment just dumped. The grain is then dumped from that compartment. The procedure is continued until all of the grain compartment 40 have been exposed to permit the grain to be dumped therefrom into individual containers.

Thus it can be seen that a novel grain probe has been described which permits grain from various depths within a storage facility to be tested inasmuch as the grain from that particular depth is maintained in a separate compartment. Thus it can be seen that the invention accomplishes at least all of its stated objectives.

We claim:

1. A grain probe, comprising,
   an elongated outer tubular member having an open upper end and a closed lower end,
   said outer tubular member having a plurality of vertically spaced-apart openings formed therein,
   an elongated inner tubular member rotatably mounted within said outer tubular member and having upper and lower ends,
   said inner tubular member having a plurality of vertically spaced-apart openings formed therein adapted to register with the openings in said outer tubular member, when said inner tubular member is rotated to a first position with respect to said outer tubular member, to permit grain to enter the interior of said inner tubular member,
   said openings in said inner tubular member being out of register with the openings in said outer tubular member, when said inner tubular member is rotated to a second position relative to said outer tubular member, to maintain the grain within said inner tubular member or to prevent grain from entering the interior of said inner tubular member,
   said inner tubular member having a partition means between pairs of adjacent openings in said inner tubular member to create a plurality of vertically spaced compartments therein,
   said inner tubular member being selectively longitudinally slidably mounted in said outer tubular member for longitudinal slidable movement only when said inner tubular member is rotated to its second position, to permit said inner tubular member to be pulled outwardly from said outer tubular member thereby successively exposing the openings in said inner tubular member to permit the grain in each of said compartments to be individually successively dumped therefrom, and
   a yieldable retaining means to selectively restrict the longitudinal movement of said inner tubular member in said outer tubular member.

2. The grain probe of claim 1 wherein the upper end of said outer tubular member has first and second, oppositely disposed slots formed therein extending downwardly from the upper end thereof and has third and fourth horizontally disposed slots formed therein which have one end thereof in communication with the lower ends of said first and second slots respectively, said inner tubular member having a pair of oppositely disposed pins extending laterally therefrom adjacent the upper end thereof which are adapted to be slidably received in said first and third slots and said second and fourth slots respectively, said first, second, third and fourth slots having a width slightly greater than said pins to guide said pins longitudinally and horizontally.

3. The grain probe of claim 2 wherein said yieldable retaining means is a tubular cap means mounted on said outer tubular member at the upper end thereof which at least partially covers said first and second slots, and does not cover said third and fourth slots, and wherein said pins extends laterally a distance so as to frictionally engage said cap during longitudinal movement of said inner tubular member.

* * * * *